United States Patent [19]

Holt

[11] 4,192,194

[45] Mar. 11, 1980

[54] METHOD AND MEANS FOR BIAXIALLY TESTING MATERIAL

[75] Inventor: Neil L. Holt, Foster City, Calif.

[73] Assignee: Anamet Laboratories, Inc., San Carlos, Calif.

[21] Appl. No.: 932,951

[22] Filed: Aug. 11, 1978

[51] Int. Cl.² ............................................. G01N 3/10
[52] U.S. Cl. .................................................... 73/794
[58] Field of Search ................................ 73/794–796, 73/37

[56] References Cited

U.S. PATENT DOCUMENTS 3,975,950  8/1976  Erdei .................................. 73/795 X

OTHER PUBLICATIONS

R. E. Ely, "Biaxial Fracture Stresses for Filled-Epoxy Tubes", *Experimental Mechanics*, pp. 492–496, (Dec. 1974).

*Handbook of Experimental Stress Analysis*, edited by Hetenyi, p. 40, (1950).

Sharma et al., "Experimental Investigation on Fracture of Visco-Elastic Materials Under Biaxial-Stress Fields", *Experimental Mechanics*, pp. 202–209, (May 1968).

*Primary Examiner*—Anthony V. Ciarlante
*Attorney, Agent, or Firm*—Flehr, Hohbach and Test

[57] ABSTRACT

A thin-wall tube specimen is biaxially tested for stress analysis by applying compressive axial stress and either internal surface pressure or external surface pressure to the specimen. Torsion is not required. The sample is positioned between platens which are assembled inside a pressure collet. Axial compressive stress is applied through the platens to the specimen, and hydraulic pressure is applied through the assembly to the internal and external cylindrical surfaces of the specimen. Rubber bladders may be employed when applying the surface pressures.

15 Claims, 7 Drawing Figures

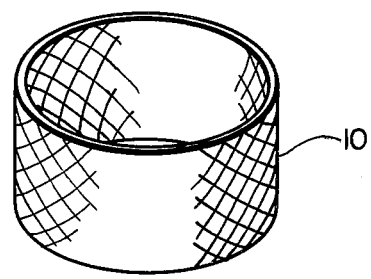
FIG.__1
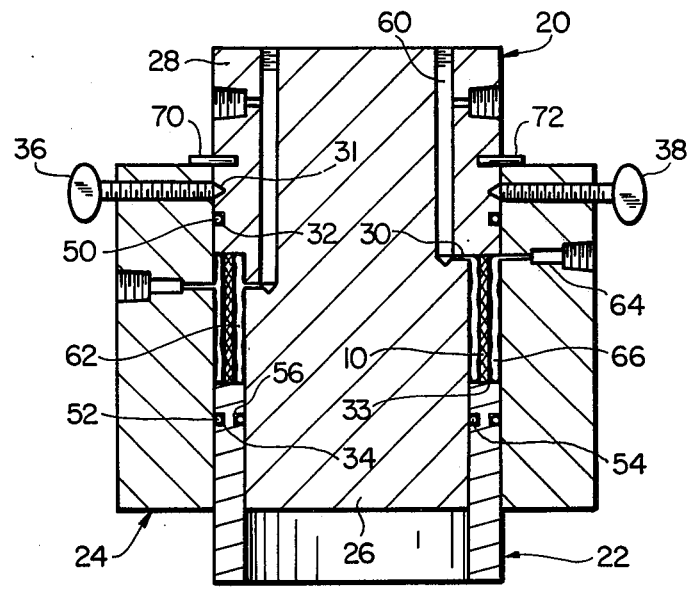
FIG.__3
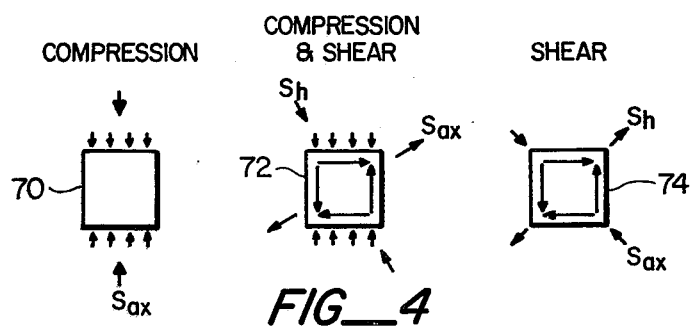
FIG.__4
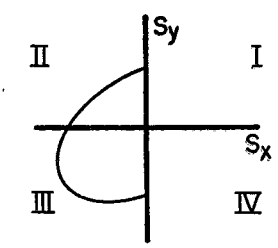
FIG.__5A
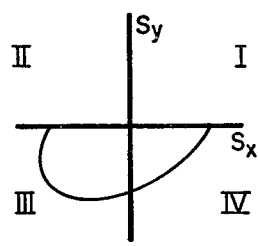
FIG.__5B
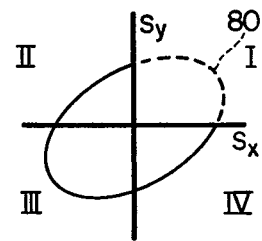
FIG.__5C

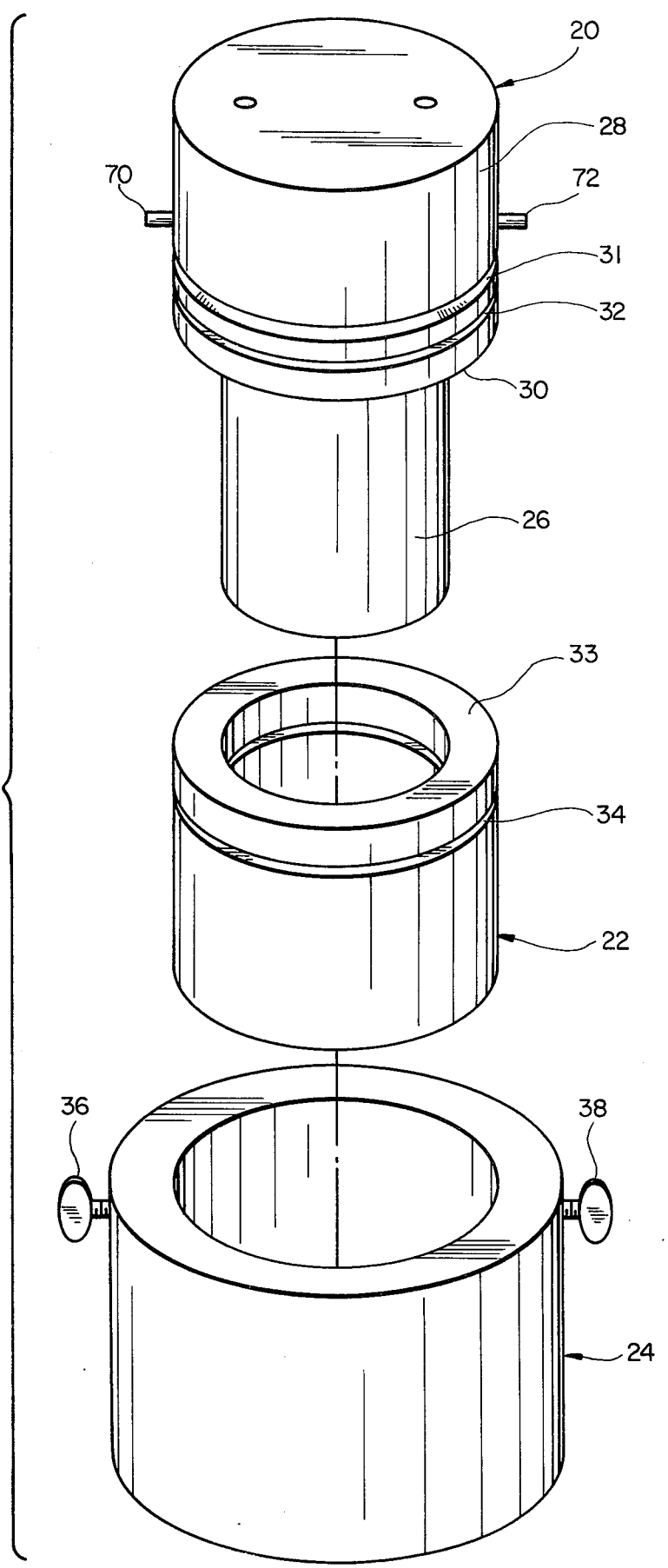
FIG_2

METHOD AND MEANS FOR BIAXIALLY TESTING MATERIAL

BACKGROUND OF THE INVENTION

This invention relates generally to stress testing of materials, and more particularly the invention relates to a method and apparatus for biaxially testing materials.

The strength of materials is measured by applying compressive and tensile stresses thereto. All possible biaxial stress states may be represented in a stress plane defining unit stress in X and Y coordinates with tensile stress being positive and compressive stress being negative. The first quadrant represents those stress states where both principal stresses are tensile. The second and fourth quadrants represent stress states where one stress is tensile and the other compressive. Quadrant three represents those stress states where both principal stresses are compressive. Pure shear is represented by a line bisecting quadrants two and four where unit stress in the X direction is equal and opposite to the unit stress in the Y direction.

When a material is subjected to certain combinations of stress it will fail. When all of these combinations are plotted on the biaxial principal stress plane, a biaxial failure envelope is generated. If a specimen is subjected to stress states lying inside of the failure envelope it will be undamaged. However, subjecting a specimen to stress states lying on or outside of the biaxial failure envelope will cause failure in the material.

Certain materials such as laminates and fiber reinforced composites exhibit anisotropic failure. A number of specimen load test systems have been used in the past to characterize the behavior of composite samples exhibiting anisotropic behavior under biaxial states of stress. One approach for characterizing laminates is the off-axis tensile test. With this test the material axis and the load direction are purposely not the same, thus the stress state relative to the material axis is biaxial. Thin wall tube specimens have been employed in testing of composites wherein rotation of the principal stress directions may be achieved by applying torques about the longitudinal axis of the tube. However, in composite or brittle materials premature failure may occur due to extraneous stresses imposed by changes in specimen sections or by the grips for applying torque. Other biaxial tests include the plate bulge test wherein a plate is hydraulically forced through a specially shaped opening, and the use of cruciform specimens.

All known prior art systems for biaxially testing a specimen have limitations in providing consistent and accurate test results.

SUMMARY OF THE INVENTION

An object of the present invention is an improved method of biaxially testing a material.

Another object of the invention is improved biaxial test apparatus.

Still another object of the invention is an improved method and test apparatus for biaxially testing a material in the second, third, and fourth stress quadrants of a biaxial stress plane.

Briefly, the method of biaxially stress testing a material in accordance with the present invention includes loading a thin wall tube or cylindrical test sample between first and second platens, applying axial stress to the sample through the first and second platens, and concurrently applying pressure to a cylindrical surface of the sample. The pressure may be applied to the internal cylindrical surface of the sample or by placing the first and second platens within collet means, pressure may be applied to the external cylindrical surface of the sample.

The test apparatus includes a first platen having an outer surface, an inner cylindrical surface, and a sample receiving surface at one end of the platen. A second platen is provided which has a cylindrical first portion for insertion into the first platen, a second portion, and a sample receiving surface on the second portion extending outwardly from the first portion. Means is provided for applying compressive force through the first and second platens to a cylindrical test sample mounted therebetween. Means is provided for applying internal pressure to the cylindrical sample when mounted between the first and second platens, and means including an outer pressure collet is provided for applying external surface pressure to a sample.

These and other objects and features of the invention will be more readily apparent from the following detailed description and appended claims when taken with the drawing.

BRIEF DESCRIPTION OF THE DRAWING

FIG. 1 is a perspective view of a test sample useful with the present invention.

FIG. 2 is an exploded perspective view of one embodiment of test apparatus in accordance with the invention.

FIG. 3 is a side view in section of a test sample and the assembled test apparatus shown in FIG. 2.

FIG. 4 is a representation of stresses produced by combinations of axial load and pressure in accordance with the invention.

FIGS. 5A–5C are stress planes with failure envelopes obtained in accordance with the present invention.

DESCRIPTION OF THE PREFERRED EMBODIMENTS

FIG. 1 is a perspective view of a test sample useful with the present invention. The sample 10 may comprise a laminated structure of composite materials such as glass filaments or graphite filaments embedded in resin matrices with the specimen shaped as a thin walled tube or cylinder having an external surface and an internal surface. The test samples are preferably short cylinders of approximately four inches in diameter. A short specimen is used because the load transfer mechanism insures uniformity of axial stress even at the stress ends. A short length is also desirable from a buckling standpoint. Wall thicknesses will vary depending upon the number and thickness of piles of composite material. When a specimen is formed from a tape for example, complimentary structures will be formed by wrapping the tape or laminate in opposite direction for the complimentary specimen. As will be described further hereinbelow, complimentary structures may be necessary to achieve a failure envelope for quadrants II, III, and IV of a biaxial stress plane.

A sample such as illustrated in FIG. 1 is tested in apparatus in accordance with the invention such as the embodiment shown in exploded view in FIG. 2. The apparatus includes an upper platen 20, a lower platen 22, and an outer pressure collet 24. The platens and collet are preferably made of hardened steel (e.g. 4344 or 300 M). Alternatively, hardened inserts may be used on the surfaces where the load is applied to a test sample.

Platen 20 includes a cylindrical bottom portion 26 and a top portion 28 with a sample receiving surface 30 on the top portion 28 extending outwardly from cylindrical portion 26. Groove 32 is provided in top portion 28 for receiving an O ring which provides a hydraulic oil seal in the assembled test apparatus, and groove 31 receives thumb screws for retaining the platens within the collet.

Platen 22 is cylindrically shaped with the outer diameter corresponding to the diameter of the top portion 28 of platen 20 and with an inner diameter corresponding to the diameter of the cylindrical portion 26 of platen 20. A groove 34 is provided in the outer surface of platen 22 for receiving an "O" ring oil seal.

Collet 24 has an inner cylindrical surface of diameter corresponding to the outer diameter of platen 22 and the diameter of the top portion 28 of platen 20 whereby the assembled platens can be inserted into collet 24. Thumbscrews 36, 38 extend through collet 24 to engage groove 31 of platen 20 and maintain the assembled platens in position during a stress test. The top platen 20 and the outer pressure collet 24 have pressure channels through which pressure is exerted on a sample during the test procedures, as will be described further hereinbelow with reference to FIG. 3.

Referring now to FIG. 3 a specimen 10 such as illustrated in FIG. 1 is shown in the cross section view of the assembled test apparatus of FIG. 2. Like elements in the several views have the same reference numerals. Test sample 10 is mounted between platen 20 and platen 22 with the top of the sample butting surface 30 of platen 20, and the bottom of the sample abutting surface 33 of platen 22. O-rings 50, 52 and 54 are provided in the grooves 32, 34 and 56 of platens 20 and 22 to provide pressure seals for the test chamber in which sample 10 is mounted. The O-ring pressure seals should provide an oil seal to maintain pressure up to 8,000 psi.

Platen 20 includes a pressure line 60 through which hydraulic pressure can be applied to the internal surface of specimen 10. Advantageously, the hydraulic line may be connected to a silicone rubber bladder 62 to insulate the test sample from the hydraulic oil used for application of pressure. However, bladder 62 is not essential to operation of the test apparatus.

Similarly, a channel 64 is provided through collet 24 for the application of pressure to the exterior surface of sample 10. Again, a silicone rubber bladder 66, similar to the bladder 62, may be connected to channel 64 to receive the hydraulic oil and apply pressure to the exterior surface of sample 10. The bladders 62 and 66 are toroidally shaped to abut the interior and exterior cylindrical surfaces, respectively, of the sample 10.

Pins 70 and 72 may be provided in upper platen 20 to limit travel thereof when inserted into collet 24 whereby thumbscrews 36 and 38 can be properly seated in groove 31 in the exterior surface of platen 20.

Metal lubricants such as a thin sheet of copper or lead are provided at either end of sample 10 in abutment with the platen surfaces to minimize restraint. The foils equalize loading of the specimen ends and compensate for slight irregularities and mismatch between the platens and the test sample. This minimizes blooms of the specimen ends, a problem frequently encountered in the compression testing of composites. The foil further insures uniformity of axial stress. Additionally, the foil prevents the silicone rubber oil bladders from extruding under the specimen ends.

In testing the specimen, the assembled platens and collet are placed in a hydraulic actuated load frame for the application of axial force. FIG. 4 illustrates schematically all of the biaxial states of stress which can be imparted to a test specimen using the apparatus in accordance with the present invention. It will be noted that in each of illustrated cases the same principal stress states may be produced by applying axial stress, $S_{ax}$ and surface pressure, $S_h$. Thus, an axial load and surface pressure can generate all of the stress states producible by an axial load and torsion without the drawback of principal axes rotation. Further, it can obtain compression—compression, a stress state unobtainable in a torsion machine. As illustrated, the unit area 70 is receiving only axial stress and experiences only compression. By adding some surface pressure with the axial stress both compression and shear is realized as shown in 72. By balancing the axial stress and surface pressure pure shear will be experienced by the sample shown at 74.

Development of a failure envelope using the test apparatus in accordance with the present invention is illustrated in FIGS. 5a–5c. In FIG. 5a a specimen is tested by the application of axial compression and both internal pressure and external pressure to develop the failure envelope in quadrants II and III of the stress plane. As above described, the failure envelope indicates the point of failure of a specimen for varying stresses. By using a complimentary sample in which filament alignment in the composite is reoriented in a complimentary direction, a failure envelope for quadrants III and IV is generated as illustrated in FIG. 5b. Thus, by combining the failure envelope from FIG. 5a, and the failure envelope from FIG. 5b, the envelope for quadrants II, III and IV is realized as shown in FIG. 5c. To complete the envelope, as shown by the dotted line 80, a sample would be subjected to stress by pulling in a conventional failure analysis test apparatus.

The method of testing a material using the apparatus in accordance with the present invention provides accurate and reproducible stress analysis without the employment of torsion to test specimens. The invention has proved particularly advantageous in the testing of composites and laminar structures.

While the invention has been described with reference to specific embodiments the description is illustrative and is not to be construed as limiting the scope of the invention. Various applications, modifications, and changes may occur to those skilled in the art without departing from the true spirit and scope of the invention as defined by the appended claims.

What is claimed is:

1. Biaxial test apparatus for cylindrical material samples comprising
   a first platen having an outer surface, an inner cylindrical surface, and a sample receiving surface at one end of said first platen,
   a second platen having a cylindrical first portion for insertion into said first platen, a second portion, and a sample receiving surface on said second portion extending outwardly from said first portion, and
   means for applying pressure to a cylindrical surface of a sample when mounted between said first platen and said second platen.

2. Biaxial test apparatus as defined by claim 1 wherein said means for applying pressure to a cylindrical surface of said test sample includes a channel in said second platen from said second portion extending into said first portion and to the cylindrical surface of said first portion.

3. Biaxial test apparatus as defined by claim 2 wherein said means for applying pressure further includes an inflatable bladder means connected to said channel at the cylindrical surface of said first portion.

4. Biaxial test apparatus as defined by claim 2 wherein said outer surface of said first platen is cylindrical, and the outer surface of said second portion of said second platen is cylindrical and of the same diameter as said outer surface of said first platen, and further including an outer pressure collet having an internal cylindrical surface for receiving said first and second platens.

5. Biaxial test apparatus as defined by claim 4 and further including means for applying external pressure to a sample when mounted between said first and second platens.

6. Biaxial test apparatus as defined by claim 5 wherein said means for applying said pressure to a cylindrical surface of a test sample includes a first inflatable bladder means and means for applying pressure to the external cylindrical surface of the test sample includes a second inflatable bladder means.

7. Biaxial test apparatus as defined by claim 1 and including means for applying compressive force through said first platen and said second platen to a sample.

8. Biaxial test apparatus as defined by claim 7 wherein said means for applying force through said first platen and said second platen to a sample comprises a hydraulic actuated load frame.

9. Biaxial test apparatus as defined by claim 8 wherein said outer surface of said first platen in cylindrical, and outer surface of said second portion of said second platen is cylindrical and of the same diameter as said outer surface of said first platen, and further including an outer pressure collet having an internal cylinder for receiving said first and second platens.

10. The method of biaxially stress testing a test sample having internal and external cylindrical surfaces comprising the steps of
(a) providing a lubricant at each end of said sample to compensate for surface irregularities and equalize loading of said sample ends,
(b) loading said sample and said lubricants between first and second platens,
(c) applying axial stress to said sample through said first and second platens, and,
(d) concurrently applying pressure to a cylindrical surface of said sample.

11. The method of biaxially testing as defined by claim 10 and further including after step (b) the step of placing said first and second platens within collet means.

12. The method of biaxially testing as defined by claim 11 wherein step (d) includes applying pressure to the external cylindrical surface of said sample.

13. The method of biaxially testing as defined by claim 11 wherein step (d) includes applying pressure to the internal cylindrical surface of said sample.

14. The method of biaxially testing as defined by claim 10 wherein step (d) includes applying pressure to the internal cylindrical surface of said sample.

15. The method of biaxially testing as defined by claim 10 wherein said lubricant comprises a low shear strength material.

* * * * *